United States Patent [19]

Vogel et al.

[11] Patent Number: 4,515,975
[45] Date of Patent: May 7, 1985

[54] CHROMAN DERIVATIVES AND THEIR PREPARATION

[75] Inventors: Friedrich Vogel, Wachenheim; Joachim Paust, Neuhofen, both of Fed. Rep. of Germany

[73] Assignee: BASF Aktiengesellschaft, Fed. Rep. of Germany

[21] Appl. No.: 439,625

[22] Filed: Nov. 4, 1982

Related U.S. Application Data

[62] Division of Ser. No. 315,856, Oct. 28, 1981, abandoned.

[30] Foreign Application Priority Data

Nov. 24, 1980 [DE] Fed. Rep. of Germany ....... 3044109

[51] Int. Cl.³ ............................................. C07D 311/22
[52] U.S. Cl. .................................... 549/411; 549/407; 549/401
[58] Field of Search ......................... 549/401, 407, 411

[56] References Cited

U.S. PATENT DOCUMENTS

| 2,274,449 | 2/1942 | John et al. ............... | 549/401 |
| 3,947,473 | 3/1976 | Scott et al. ............... | 549/407 |
| 4,097,495 | 6/1978 | Chan et al. ............... | 549/407 |
| 4,113,740 | 9/1978 | Cohen et al. .............. | 549/407 |
| 4,127,608 | 11/1978 | Olson et al. .............. | 549/407 |
| 4,179,447 | 12/1979 | Connor et al. ............ | 549/401 |
| 4,280,011 | 7/1981 | De Simone ............... | 549/372 |

FOREIGN PATENT DOCUMENTS 1506076 4/1978 United Kingdom ................ 549/401

OTHER PUBLICATIONS

G. P. Ellis, "Chromenes, Chromanones and Chromones", John Wiley & Sons, New York, N.Y. 1977, pp. 70–71, 157–159, 182–184, 301–307 and 331.

McOmie, Advances in Organic Chemistry, vol. 3, Interscience Publishers, New York, N.Y. 1963, pp. 216–219, 230–231, 262–265.

Mayer et al., Helv. Chim. Acta, 46, 650 (1963).

*Primary Examiner*—Nicky Chan
*Attorney, Agent, or Firm*—Keil & Weinkauf

[57] ABSTRACT

Chroman derivatives of the general formula I

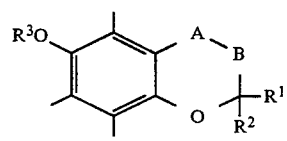

I where A—B is —$CH_2$—$CH_2$—(Ia), —CH=CH—(Ib), —CHOH—$CH_2$—(Ic) or —CO—$CH_2$—(Id), $R^1$ is —$CH_2$—O—R' or

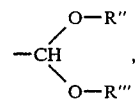

where R' is $C_1$–$C_4$-alkyl or arylmethyl and R" and R''' are each $C_1$–$C_4$-alkyl, which can also be bonded to form a five-membered or six-membered cyclic acetal, $R^2$ is $C_1$–$C_4$-alkyl and $R^3$ is H or a protective group.

2 Claims, No Drawings

CHROMAN DERIVATIVES AND THEIR PREPARATION

The subject application is a division of application Ser. No. 315,856 which was filed on Oct. 28, 1981 now abandoned.

The present invention relates to novel chroman derivatives of the general formula I

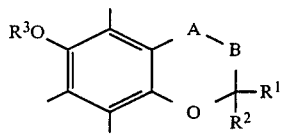

where A—B is —$CH_2$—$CH_2$— (Ia), —CH=CH— (Ib), —CHOH—$CH_2$— (Ic) or —CO—$CH_2$— (Id), $R^1$ is —$CH_2$—O—R' or

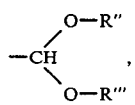

where R' is $C_1$–$C_4$-alkyl or arylmethyl and R" and R''' are each $C_1$–$C_4$-alkyl, which can also be bonded to form a five-membered or six-membered cyclic acetal, $R^2$ is $C_1$–$C_4$-alkyl and $R^3$ is H or a protective group.

The present invention also relates to the preparation of the 2-hydroxymethyl- and 2-formyl-chroman derivatives IIa and IIb

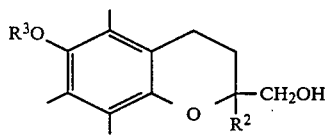

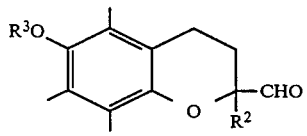

The compounds IIa and IIb are important components for the synthesis of α-tocopherol III

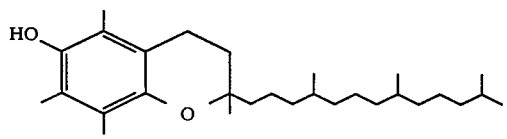

and its 2-alkyl-homologs, for example by converting the methylol in IIa to halomethyl and coupling the sidechain of the tocopherol to the halomethyl-chroman derivative by a Grignard reaction, or by reacting IIb with a 3,7,11-trimethyldodecylphosphonium salt to give III (H. Mayer et al., Helv. Chim. Acta, (1963), Volume 46, pages 650 et seq.).

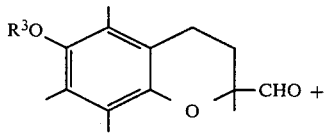

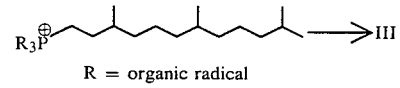

R = organic radical

Since it has hitherto been extremely difficult to obtain the formylchromans IIb and hence also their reduction products the hydroxymethylchromans IIa (cf. H. Mayer et al., page 652), it is an object of the present invention to make these compounds more readily accessible.

We have found that this object is achieved and that the 2-hydroxymethylchromans and the 2-formylchromans of the general formulae IIa and IIb

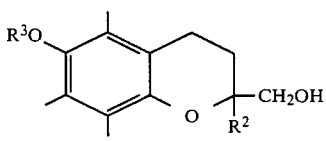

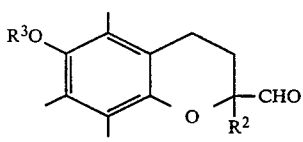

where $R^2$ is $C_1$–$C_4$-alkyl and $R^3$ is hydrogen or a protective group, are obtained by (a) reacting acetyl-trimethylhydroquinone IV

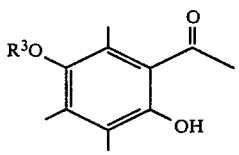

with a ketone of the general formula V

$R^3$—CO—$R^1$      V where $R^1$ is —$CH_2$—O—R' or

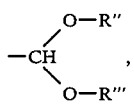

where R' is $C_1$–$C_4$-alkyl or arylmethyl and R" and R''' are each $C_1$–$C_4$-alkyl which can also be bonded to form a five-membered or six-membered cyclic acetal, in the presence of a base to give a chroman derivative Id

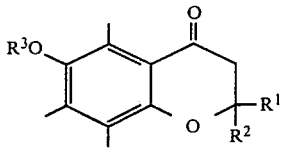

(b) hydrogenating Id under dehydrating conditions to give Ia

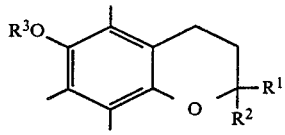

and (c) converting $R^1$ in Ia to hydroxymethyl by hydrolysis or to formyl by hydrogenolysis.

The acetyl-trimethylhydroquinone used as the starting compound IV is known and can advantageously be obtained, for example, from trimethylhydroquinone and acetyl chloride by a Friedel-Crafts synthesis.

The ketones V, where they are not already known, can be obtained in a conventional manner. For example, the alkyl alkoxymethyl ketones Va $$R^2-CO-CH_2-O-R' \qquad \text{Va}$$

can be prepared by etherifying alkan-2-on-1-ols. Since the alkoxy (—O—R') is in any case split off again hydrolytically or hydrogenolytically in the course of most further syntheses, and in particular during the preparation, according to the invention, of the compounds IIa and IIb, R' is of course preferably a group which can easily be split off, such as methyl, benzyl or tert.-butyl.

The alkyl dialkoxymethyl ketones Vb

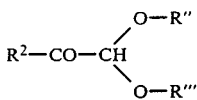

can be obtained, for example, by the processes of German Laid-Open Application DOS No. 1,252,193 and German Published Application DAS No. 2,247,345. R' is, in particular, methyl or benzyl. R'' and R''' are preferably methyl or the 1,2-ethylene, 1,2-propylene, 1,3-propylene or, in particular, 2,2-dimethyl-1,3-propylene radical. $R^2$ in the compounds V and hence in the compounds I is preferably ethyl or, in particular, methyl.

It is surprising that the cyclizing aldol condensation of IV with Va or, in particular, Vb proceeds smoothly. German Laid-Open Application DOS No. 2,611,910 discloses the preparation of chroman derivatives by reacting IV with carbonyl compounds containing no reactive groups other than the carbonyl group, but not by reaction with bifunctional compounds such as the alkoxy-ketones Va and the glyoxal derivatives Vb.

IV is reacted with V in the presence of a base, suitable examples of the latter being inorganic bases, such as NaOH, KOH, Na methylate and K methylate in amounts of from 1 to 2 moles per mole of IV and, in particular, organic amines in amounts of from 1 to 5 moles per mol of IV. Secondary amines, such as pyrrolidine, piperidine, morpholine and dimethylamine, are particularly preferred.

The reaction can be carried out without a solvent, but the use of an inert organic solvent, such as toluene, benzene, tetrahydrofuran, carbon tetrachloride or xylene, in an amount of from about 2 to 5 l per kg of IV, is preferred. The reaction is advantageously carried out at from about 50° to 150° C. It is advisable for the water liberated during the reaction to be distilled off continuously from the reaction mixture, for example azeotropically with the solvent. It is also advantageous to carry out the reaction under an inert gas atmosphere, since the acetyl-trimethylhydroquinone oxidizes readily.

The ratio of IV to V is preferably from 1:1 to 0.5:1.

In a particular embodiment of process step (a), an optically active amine is used as the base since this favors formation of one of the two enantiomers of Id, where the 2-C atom is a center of asymmetry, and synthesis of optically pure α-tocopherol is thereby facilitated.

In process step (b), the chromanones Id are hydrogenated to the chromans Ia under dehydrating conditions in a conventional manner, for example with metal hydrides, such as diisobutyl aluminum hydride or LiAlH$_4$, or with hydrogen under from 50 to 300 bar and at from 50° to 250° C. in the presence of a noble metal catalyst, such as Pd or Pt, or of Raney nickel.

It is also possible to convert Id to Ia in steps, by first hydrogenating Id with a metal hydride, such as NaBH$_4$, or with hydrogen in the presence of one of the above hydrogenation catalysts to give the 4-hydroxychroman (Ic), dehydrating this in a conventional manner, for example by means of treatment with acid or by the action of heat, to give the chrom-3-ene (Ib) and catalytically hydrogenating the latter with hydrogen, Ia, also in a conventional manner in the presence of an inert solvent, to give Ia.

The reaction steps from Id to Ia are as follows:

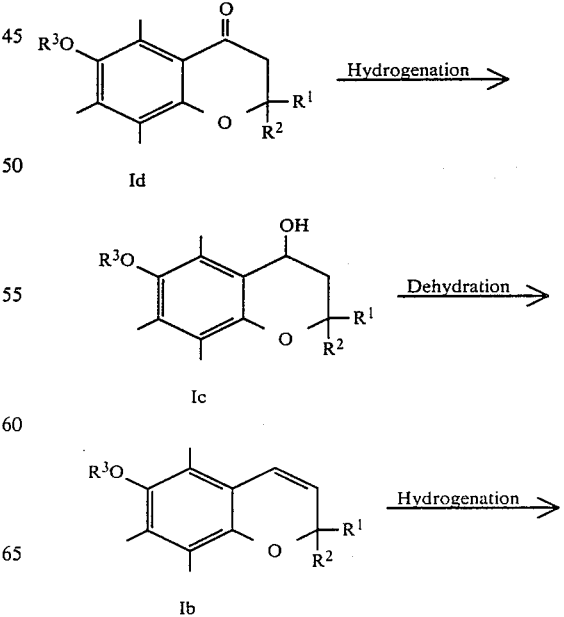

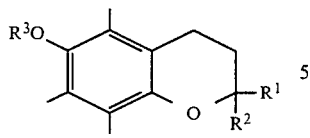

In process step (c), the ether radical or the acetal groups in the compounds Ia are then split off, also in a conventional manner, for example by treatment with mineral acids in aqueous solution, to give the 2-hydroxymethyl-chromans IIa or 2-formyl-chromans IIb.

The free 6-hydroxy compound or acetyltrimethylhydroquinone protected by $R^3$ can be used in the synthesis starting from IV. If the unprotected compound is used ($R^3 =H$), $R^3$ can be introduced in a conventional manner at any stage of the synthesis and, if desired, can also be split off again hydrolytically or hydrogenolytically. As is generally known, examples of suitable protective groups $R^3$ are $C_1$–$C_4$-alkyl, such as methyl, arylmethyl, such as benzyl, tri-($C_1$–$C_4$-alkyl)-silyl, such as trimethylsilyl, $C_1$–$C_4$-acyl, such as acetyl, tetrahydropyran-2-yl and 4-methyl-5,6-dihydro-2-H-pyran-2-yl. Of these, acetyl, benzyl and tert.-butyl are preferred.

The compounds I(Ia-Id) are valuable intermediates for the synthesis of α-tocopherol (vitamin E) and its derivatives. One important synthesis route is via the compounds IIa or IIb, but it is also possible to introduce the side chain of tocopherol into the compounds Ib, Ic or Id and then to carry out the operations required for the preparation of the compounds having the chroman structure.

EXAMPLES

All operations were carried out under an argon atmosphere.

EXAMPLE 1

Preparation of 2-ethyl-2-(5′,5′-dimethyl-1′,3′-dioxan-2′-yl)-6-hydroxy-5,7,8-trimethylchroman-4-one

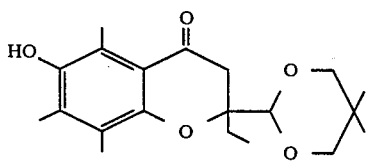

3.00 g (15.6 mmoles) of acetyl-trimethylhydroquinone, 3.10 g (6.18 mmoles) of 5,5-dimethyl-2-(propion-1′-yl)-1,3-dioxane, in the presence of 2.50 g (30 mmoles) of pyrrolidine and 45 ml of toluene were heated at the boil for 3 hours, during which the water formed was continuously removed as a water/toluene azeotrope.

The reaction mixture was then poured onto ice-water and adjusted to pH 3 with dilute hydrochloric acid, after which the product was extracted with methylene chloride in a conventional manner and isolated from the extract phase. Boiling point: 250° C. (bulb tube); white crystals of melting point 141° C.; yield: 76%.

EXAMPLE 2

Preparation of 2-(dimethoxymethyl)-6-hydroxy-2,5,7,8-tetramethyl-chroman-4-one

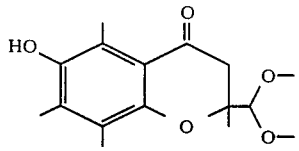

15.0 g (77 mmoles) of acetyl-trimethylhydroquinone, 10.5 g (89 mmoles) of 1,1-dimethoxy-propan-2-one and 9.30 g (131 mmoles) of pyrrolidine were reacted in toluene solution by a method similar to that of Example 1 to give the above product. Boiling point: 165°–170° C./$6.10^{-5}$ mbar (bulb tube); yield: 70%.

EXAMPLE 3

Preparation of 6-hydroxy-2-methoxymethyl-2,5,7,8-tetramethyl-chroman-4-one

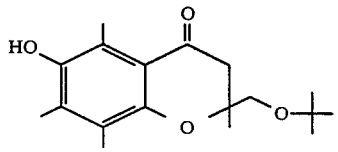

3.00 g (15.6 mmoles) of acetyl-trimethylhydroquinone, 1.58 g (18 mmoles) of methoxyacetone and 250 g (30 mmoles) of pyrrolidine were reacted in toluene solution by a method similar to that of Example 1 to give the above product, which was obtained as an oil. Boiling point: 250°–270° C. (bulb tube); yield: 37%.

EXAMPLE 4

Preparation of 2-tert.-butoxymethyl-6-hydroxy-2,5,7,8-tetramethyl-chroman-4-one 1.00 g (5.2 mmoles), 1.01 g (7.8 mmoles) of tert.-butoxyacetone and 0.92 g (13 mmoles) of pyrrolidine were reacted with toluene solution by a method similar to that of Example 1 to give the above product, which was obtained as a crude oil (bulb tube); yield: 19%; IR: 3,600, 1,720 cm$^{-1}$.

EXAMPLE 5

Preparation of optically enriched 6-acetoxy-2-(dimethoxymethyl)-2,5,7,8-tetramethyl-chroman-4-one

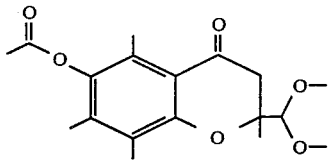

1.00 g (5.2 mmoles) of acetyl-trimethylhydroquinone, 0.71 g (6 mmoles) of 1,1-dimethoxypropanone, in the presence of 1.65 g (10 mmoles) of (L)-phenylalanine and 20 ml of acetonitrile and 2 g of a 4-Å-molecular sieve (to bond the water of reaction) were stirred under reflux for 100 hours.

The crude 6-hydroxy compound obtained when the reaction mixture was worked up was acetylated in a conventional manner with 1.5 g of acetic anhydride in a base mixture of 5 ml of pyridine and 0.5 g of 4-(N,N-dimethylamino)-pyridine. Dilute hydrochloric acid was added to the resulting mixture, after which the product was extracted with ether and isolated from the extract phase in a conventional manner. Bulb tube distillation at 250° C./4.10$^{-5}$ mbar gave 0.62 g of a partially crystalline oil (54% of theory), which was purified by chromatography on 120 g of silica gel using a 50/50 mixture of ethyl acetate and hexane. White crystals of melting point 100°-101° C. were obtained.

From the optical rotation $[\alpha]_D^{25}$ of 0.51° (c=2.12/CH$_2$Cl$_2$), it can be concluded that one of the chroman enantiomers is optically enriched, as a result of optical induction by the chiral base.

EXAMPLE 6

Preparation of 2-(dimethoxymethyl)-4,6-dihydroxy-2,5,7,8-tetramethylchroman

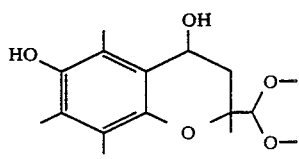

9.4 g (32 mmoles) of the product from Example 2 were reacted with 2.43 g (64 mmoles) NaBH$_4$ in 100 ml of methanol at 20°-60° C. After 6 hours, a further 2.43 g of NaBH$_4$ were added, after which the reaction mixture was stirred at room temperature for 16 hours. 100 ml of 3N NaOH were then added, and the mixture was neutralized with dilute hydrochloric acid and then extracted with ether, a brown oil being obtained as the crude product in 95% yield. IR: 3,600 (broad) cm$^{-1}$.

EXAMPLE 7

Preparation of 2-(dimethoxymethyl)-6-hydroxy-2,5,7,8-tetramethyl-chrom-3-ene

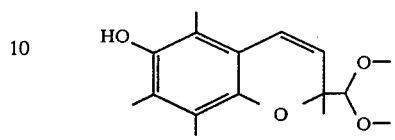

8.9 g (30 mmoles) of the 4-hydroxychroman obtained in Example 6 were distilled twice in a bulb tube at 150°-200° C./10$^{-3}$ mbar. A yellow, partially crystalline oil was obtained (53% yield), and was purified by chromatography on Al$_2$O$_5$ using a mixture of 2 parts of ether and 1 part of hexane. Melting point: 105°-107° C.

EXAMPLE 8

Preparation of 2-(dimethoxymethyl)-6-hydroxy-2,5,7,8-tetramethyl-chroman

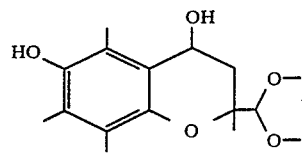

9.4 g (32 mmoles) of the product from Example 2 were reacted with 2.43 g (64 mmoles) of NaBH$_4$ in 100 ml of methanol at 20°-60° C. After 6 hours, a further 2.43 g of NaBH$_4$ were added, after which the reaction mixture was stirred at room temperature for 16 hours. 100 ml of 3N NaOH were then added, and the mixture was neutralized with dilute hydrochloric acid and then extracted with ether, a brown oil being obtained as the crude product in 95% yield. IR: 3,600 (broad) cm$^{-1}$.

EXAMPLE 7

Preparation of 2-(dimethoxymethyl)-6-hydroxy-2,5,7,8-tetramethyl-chrom-3-ene

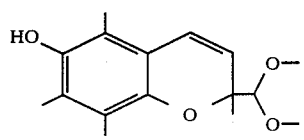

8.9 g (30 mmoles) of the 4-hydroxychroman obtained in Example 6 were distilled twice in a bulb tube at 150°-200° C./10$^{-3}$ mbar. A yellow, partially crystalline oil was obtained (53% yield), and was purified by chromatography on Al$_2$O$_3$ using a mixture of 2 parts of ether and 1 part of hexane. Melting point: 105°-107° C.

EXAMPLE 8

Preparation of
2-(dimethoxymethyl)-6-hydroxy-2,5,7,8-tetramethyl-chroman

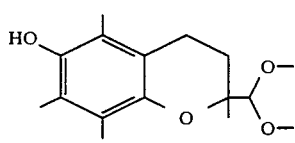

1.74 g (0.63 mmole) of the chromene obtained in Example 7 were hydrogenated in 30 ml of methanol at room temperature and under atmospheric pressure using 0.15 g of a supported catalyst comprising 10% by weight of Pd on active charcoal, in the course of 16 hours. Conventional working up gave the above compound, in 97% yield, as white crystals of melting point 102°–106° C.

EXAMPLE 9

Preparation of
6-benzyloxy-2-(dimethoxymethyl)-2,5,7,8-tetramethyl-chroman

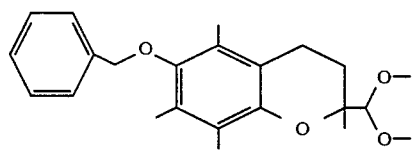

1.47 g (5.25 mmoles) of the chroman obtained in Example 8 were heated at 100° C. with 3.2 g of benzyl bromide, 1.5 g of Na₂CO₃ and 7 ml of dimethylformamide for 13 hours, and water was then added. This mixture was extracted with heptane, after which the crude product obtained from the extract phase was chromatographed on 50 g of silica gel using a mixture of 1 part by volume of ether and 2 parts by volume of heptane. The following fractions were obtained: F1=1.28 g; F2 (mixed fraction)=0.13 g; F3 (starting material)=0.23 g.

Fractions F1 and F2 were chromatographed again on 100 g of silica gel, the above product being obtained, in 64% yield, as white crystals of melting point 46°–48° C.

EXAMPLE 10

Preparation of
6-benzyloxy-2-formyl-2,5,7,8-tetramethyl-chroman

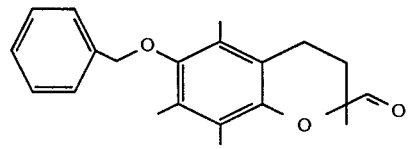

A mixture of 0.16 g (0.43 mmole) of the compound obtained in Example 9, 4 ml of ether and 2 ml of concentrated hydrochloric acid was heated at 40° C. for 2 hours and then diluted with ether and washed with aqueous NaHCO₃ solution. The above compound was isolated in a conventional manner from the organic phase which remained; yield: 48%.

EXAMPLE 11

Preparation of
2-(dimethoxymethyl)-6-hydroxy-2,5,7,8-tetramethyl-chroman (for the formula, cf. Example 8)

0.50 g (1.7 mmoles) of the chromanone obtained as described in Example 2 was hydrogenated under 250 bar and at 180° C. in the presence of 1 g of Raney nickel over 2 hours. Purification of the crude product by chromatography gave the above chroman whose properties agreed with those of the product of Example 8.

EXAMPLE 12

Preparation of
6-benzyloxy-2-tert.-butoxymethyl-2,5,7,8-tetramethyl-chroman-4-one

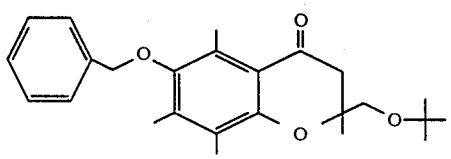

3.5 g of the crude product from Example 4 were converted to the above chromanone, using 7 g of benzyl bromide, 3 of Na₂CO₃ and 15 ml of dimethylformamide, by a method similar to that of Example 9. Yield (after purification three times by chromatography): 20%; melting point: 51°–62° C.

EXAMPLE 13

Preparation of
6-benzyloxy-2-hydroxymethyl-2,5,7,8-tetramethylchroman

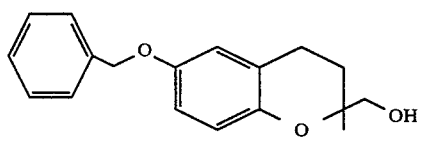

0.90 g (2.20 mmoles) of the chromanone obtained in Example 12 was converted to the 2-tert.-butoxy-methyl-chroman derivative by a method similar to that of Examples 6–8. The resulting crude product was stirred with trifluoroacetic acid at 0° C. for 2 hours, and the mixture was then poured onto 50 ml of ice-water and extracted with 50 ml of methylene chloride. Purification by chromatography gave the above compound as white crystals of melting point 65°–68° C.; yield: 30%.

We claim:

1. A process for the preparation of a 2-hydroxymethylchroman or a 2-formylchroman of the formula IIa or IIb

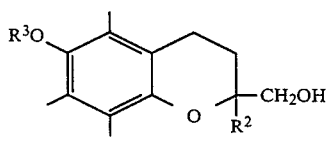

IIa

-continued

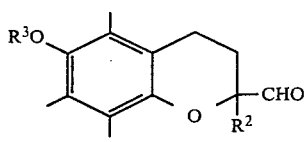
IIb where $R^2$ is $C_1$–$C_4$-alkyl and $R^3$ is hydrogen or a protective group, which comprises (a) reacting acetyl-trimethylhydroquinone IV

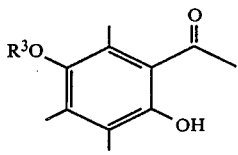
IV with a ketone of the formula V

V where $R^1$ is —$CH_2$—O—R′ or

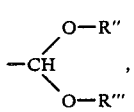

where R′ is $C_1$–$C_4$-alkyl or arylmethyl and R″ and R‴ are each $C_1$–$C_4$-alkyl, which can also be bonded to form a five-membered or six-membered cyclic acetal, in the presence of an optically active amine to give a chroman derivative Id

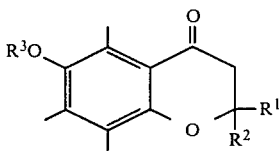
Id (b) hydrogenating Id under dehydrating conditions to give Ia

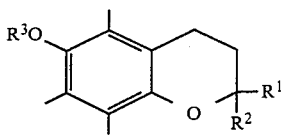
Ia and (c) converting $R^1$ in Ia to hydroxymethyl, if $R^1$ is —$CH_2$—O—R′, or to formyl, if $R^1$ is

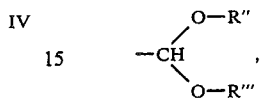

by hydrolysis or hydrogenolysis.

2. The process of claim 1, wherein the compound (Ia) is formed by hydrogenating the chroman derivative (Id) with a metal hydride or with hydrogen in the presence of a hydrogenation catalyst to form the chroman derivative (Ic)

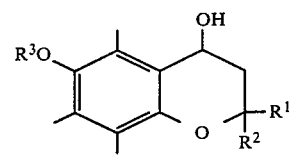
Ic and wherein the chroman derivative (Ic) is dehydrated by the action of heat or catalytically by means of an acid to form the chroman derivative (Ib)

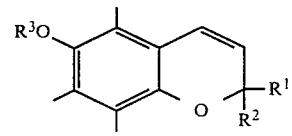
Ib whereupon the chroman derivative (Ib) is hydrogenated with hydrogen in the presence of a hydrogenation catalyst to form the chroman derivative (Ia).

* * * * *